United States Patent
Goel et al.

(10) Patent No.: US 8,734,497 B2
(45) Date of Patent: May 27, 2014

(54) REMOVABLE ANCHORING PEDICLE SCREW

(75) Inventors: Vijay K. Goel, Holland, OH (US);
Aaron Matyas, Maumee, OH (US)

(73) Assignee: The University of Toledo, Toledo, OH (US)

( * ) Notice: Subject to any disclaimer, the term of this patent is extended or adjusted under 35 U.S.C. 154(b) by 280 days.

(21) Appl. No.: 13/254,961

(22) PCT Filed: Mar. 12, 2010

(86) PCT No.: PCT/US2010/027192
§ 371 (c)(1),
(2), (4) Date: Dec. 23, 2011

(87) PCT Pub. No.: WO2010/105196
PCT Pub. Date: Sep. 16, 2010

(65) Prior Publication Data
US 2012/0109222 A1     May 3, 2012

Related U.S. Application Data (60) Provisional application No. 61/159,910, filed on Mar. 13, 2009.

(51) Int. Cl.
*A61B 17/04* (2006.01)
*A61B 17/86* (2006.01)
*A61F 2/08* (2006.01)

(52) U.S. Cl.
USPC .......................................... 606/310; 606/313

(58) Field of Classification Search
USPC ........ 606/310, 313, 326, 327; 411/17, 24, 34, 411/44, 54, 60.2, 80.1, 82.3
See application file for complete search history.

(56) References Cited

U.S. PATENT DOCUMENTS

| | | | |
|---|---|---|---|
| 5,209,753 A * | 5/1993 | Biedermann et al. | 606/304 |
| 5,713,904 A | 2/1998 | Errico et al. | |
| 5,797,963 A * | 8/1998 | McDevitt | 606/232 |
| 5,814,046 A | 9/1998 | Hopf | |
| 5,944,720 A | 8/1999 | Lipton | |
| 6,077,262 A | 6/2000 | Schlapfer et al. | |
| 6,565,567 B1 | 5/2003 | Haider | |
| 6,668,688 B2 | 12/2003 | Zhao et al. | |
| 6,827,719 B2 | 12/2004 | Ralph et al. | |
| 6,840,940 B2 | 1/2005 | Ralph et al. | |
| 7,163,539 B2 | 1/2007 | Abdelgany et al. | |
| 7,445,627 B2 | 11/2008 | Hawkes et al. | |
| 2002/0165544 A1 * | 11/2002 | Perren et al. | 606/63 |
| 2003/0000350 A1 | 1/2003 | Zhao et al. | |
| 2006/0052788 A1 | 3/2006 | Thelen et al. | |
| 2008/0288003 A1 | 11/2008 | McKinley | |
| 2009/0105771 A1 | 4/2009 | Lei et al. | |
| 2009/0131992 A1 | 5/2009 | Greenhalgh et al. | |
| 2009/0192552 A1 | 7/2009 | Andersen et al. | |

* cited by examiner

*Primary Examiner* — Andrew Yang
(74) *Attorney, Agent, or Firm* — MacMillan, Sobanski & Todd, LLC

(57) ABSTRACT

A removable anchoring pedicle screw includes an implant mounting screw, an anchor screw, and a nose piece. The anchor screw is configured to be rotated relative to the implant mounting screw such that the nose piece engages an expandable anchor. The expandable anchor is disposed between the implant mounting screw and the nose piece such that rotation of the anchor screw relative to the implant mounting screw causes expansion of the expandable anchor.

20 Claims, 6 Drawing Sheets

REMOVABLE ANCHORING PEDICLE SCREW

CROSS-REFERENCE TO RELATED APPLICATIONS AND STATEMENT REGARDING FEDERALLY SPONSORED RESEARCH

The invention claims the benefit of U.S. Provisional Patent Application Ser. No. 61/159,910, filed Mar. 13, 2009, the disclosure of which is incorporated herein by reference in its entirety. This invention was made with no U.S. Government support and the U.S. Government has no rights in this invention.

BACKGROUND OF THE INVENTION

There is no admission that the background art disclosed in this section legally constitutes prior art.

Spinal implants can be anchored to the cancellous bone within vertebrae with the use of pedicle screws. With aging patients, conditions such as osteoporosis can cause deterioration of the cancellous bone within vertebrae resulting in a loosening or backing-out of the pedicle screws. Pedicle screws that loosen or back-out can cause displacement of the spinal implant, thereby resulting in pain in the neck and upper and lower extremities and alignment problems.

Under certain conditions, it can be desirable to remove or change the spinal implant. In these situations, the pedicle screw needs to be removed and potentially reinstalled.

What is needed is a pedicle screw that firmly anchors a spinal implant to the cancellous bone within vertebrae, yet which can be easily removed once installed. The invention provides an improved pedicle screw.

SUMMARY OF THE INVENTION

In a first aspect, there is provided herein a removable anchoring pedicle screw assembly for fixing an implant to a vertebra. The removable anchoring pedicle screw comprises an implant mounting screw, an anchor screw, and a nose piece. The implant mounting screw includes a threaded bore. The anchor screw is configured to engage the threaded bore for rotation relative to the implant mounting screw. The nose piece has a threaded aperture configured to engage the anchor screw. An expandable anchor has a bore that is configured to engage the anchor screw. The expandable anchor is disposed between the implant mounting screw and the nose piece such that rotation of the anchor screw relative to the implant mounting screw causes expansion of the expandable anchor.

In another aspect, a removable anchoring pedicle screw includes an implant mounting screw having a threaded portion configured to engage an implant device. The implant mounting screw further includes a first load face and the nose piece includes a second load face, the first and second load faces engage opposite ends of the expandable anchor such that a compressive load exerted by the first and second load faces causes the expansion of the expandable anchor.

In another aspect, a removable anchoring pedicle screw assembly includes an expandable anchor having a plurality of slots that define anchoring arms. The anchoring arms are configured to deflect radially outwards from the anchor screw in response to rotation of the anchor screw relative to the implant mounting screw. The expandable anchor may cooperate with the anchor screw to define a cavity. In yet another aspect, the expandable anchor may include a cavity containing a filler material. The expandable anchor may be a frangible structure that permits the filler material to exit the expandable anchor when compressed.

In another aspect, there is provided herein a method of securing a spinal implant to vertebra. The method includes the steps of providing a removable anchoring pedicle screw assembly having an implant mounting screw, an anchor screw, a nose piece, and an expandable anchor. The method further includes drilling an aperture into a portion of a vertebra, inserting the pedicle screw assembly, nose piece first, into the aperture with the expandable anchor in a collapsed condition, rotating implant mounting screw and the anchor screw together to thread the pedicle screw assembly into the vertebra, rotating the anchor screw relative to the implant mounting screw to compress the expandable anchor thereby deploying the anchoring arms, and attaching an implant device.

Other systems, methods, features, and advantages of the invention will be or will become apparent to one with skill in the art upon examination of the following drawings and detailed description. It is intended that all such additional systems, methods, features, and advantages be included within this description, be within the scope of the invention, and be protected by the accompanying claims.

BRIEF DESCRIPTION OF THE DRAWINGS

The following drawings may contain hidden features or elements shown in dotted lines and may include phantom views of various components or elements shown in dashed-dotted lines.

DETAILED DESCRIPTION OF THE PREFERRED EMBODIMENT

Figure 1:
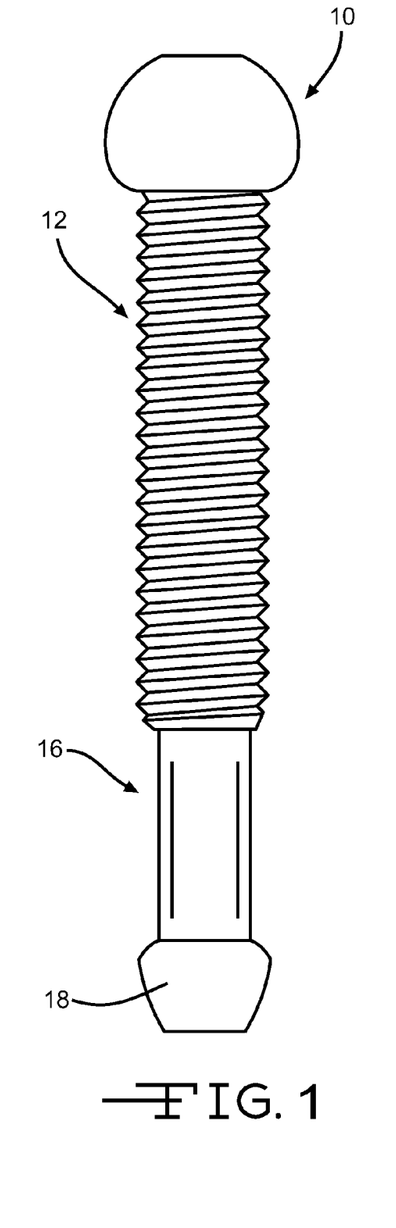
FIG. 1 is an elevational view of an embodiment of a pedicle screw assembly in an installation configuration.

Referring now to the drawings, there is illustrated in FIG. 1 an embodiment of a removable anchoring pedicle screw assembly, shown generally at 10. The pedicle screw assembly 10 is configured to anchor a spinal implant, such as a plate or rod "I" in FIGS. 4 and 5, to spinal vertebrae. The pedicle screw assembly 10 also provides for easy removal of all or only a portion of the assembly 10 from the vertebrae. The term "vertebrae" as used herein, is defined to mean any structure, portion, or part of a spinal vertebra or multiple vertebrae, including but not limited to cancellous bone, processes, bodies, facets, tubercles, pedicles and lamina.

Figure 2:
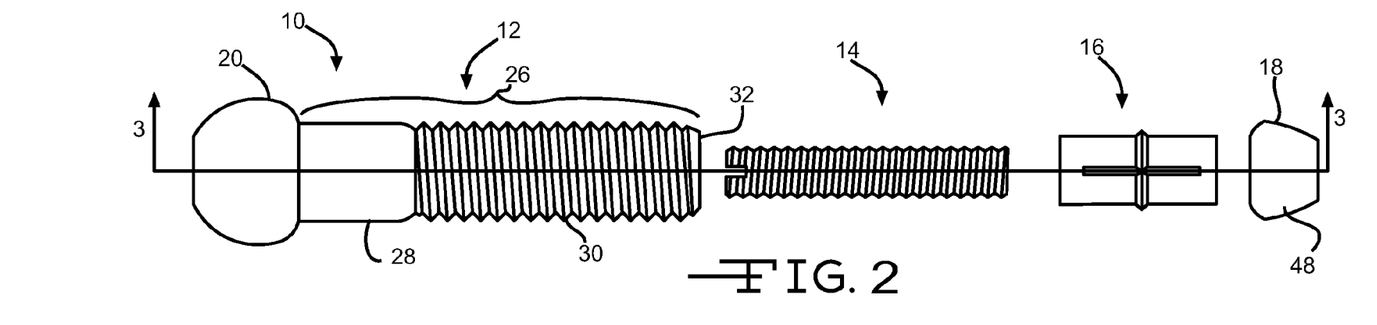
FIG. 2 is an exploded, elevational view of an embodiment of a pedicle screw.
Figure 3:
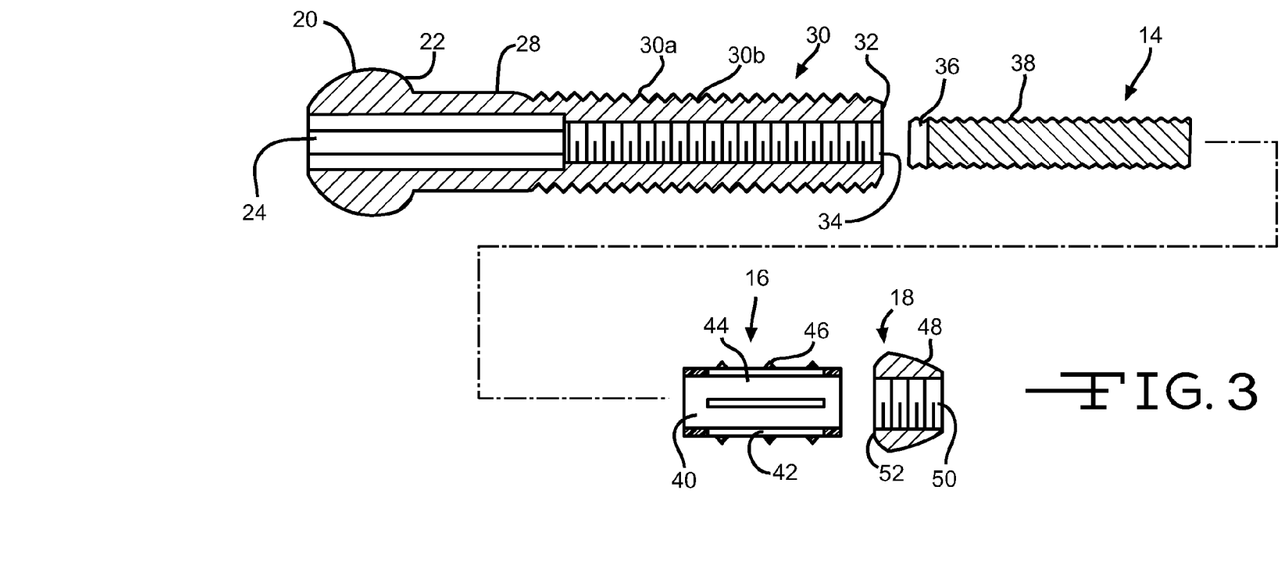
FIG. 3 is an elevational view taken along line 3-3, in cross section, of the pedicle screw of FIG. 2.

As shown in FIGS. 2 and 3, the pedicle screw assembly 10 includes an implant mounting screw 12, an anchor screw 14, an expandable anchor 16, and a nose piece 18. The implant mounting screw 12 includes a head 20 having a retainer 22 and a drive socket 24, and a main body 26. The retainer 22 is illustrated as a swivel knob having a rounded profile that permits a spinal implant device to be positioned at various orientations relative to the main body 26. However, the retainer 22 may be any shape desired or may be omitted. The drive socket 24 is illustrated as a hexagonally shaped counterbore. The drive socket 24 may be any torque transmitting shape that permits the implant mounting screw 12 to be rotated relative to the anchor screw 14.

Figure 4:
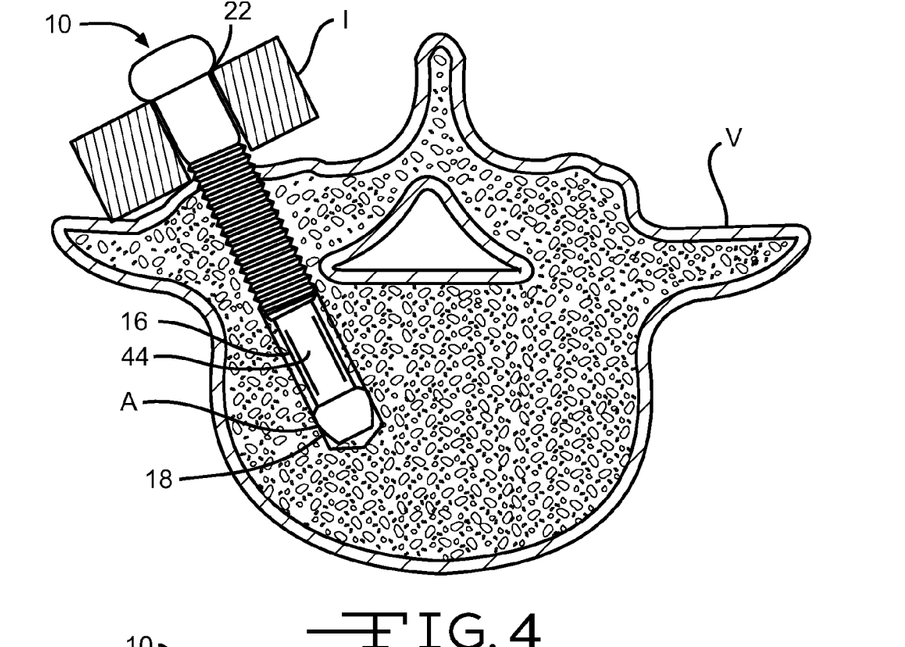
FIG. 4 is a plan elevational view of an embodiment of a pedicle screw assembly inserted into a spinal vertebra.
Figure 5:
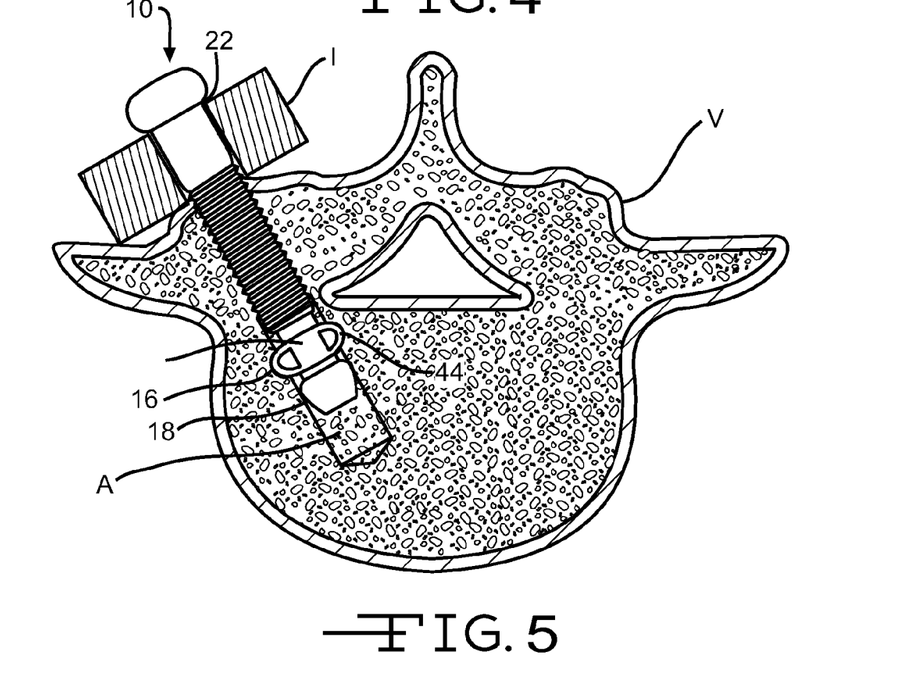
FIG. 5 is a plan elevational view of the pedicle screw of FIG. 4 moved into a deployed position.

The main body 26 of the implant mounting screw 12 is illustrated having a shoulder 28, a threaded section 30, and an anchor load face 32. The shoulder 28 is an optional feature of the pedicle screw 10 and is configured as a smooth profiled section that transitions between the retainer 22 and the threaded section 30. The shoulder 28 is illustrated having a diameter that is larger than at least either a thread crest 30*a* or a thread root 30*b* of the threaded section 30. In an embodiment of the implant mounting screw 12 having no retainer 22, the shoulder 28 may be omitted or may be smaller than the thread root 30*b* of the threaded section 30 such that a retaining nut (not shown) may be used to secure the implant I to the implant mounting screw 12, as best shown in FIGS. 4-5. The threaded section 30 may be configured to engage both a vertebra V and the retaining nut to secure the implant in place. Alternatively, the threaded section 30 may be configured to only engage the vertebra V, as shown in FIGS. 4 and 5, and the retainer 22 secures the implant I.

Referring again to FIGS. 2-3, the anchor load face 32 is configured to axially compress the expandable anchor 16 against the nose piece 18, as will be explained below. The main body 26 further includes a threaded bore 34 that is configured to engage the anchor screw 14. The anchor screw 14 includes a drive end 36 that is configured to be engaged by a key, such as a slotted end screw driver, and to rotate the anchor screw 14 within the threaded bore 34. The drive end 36 may be any suitable torque transmitting feature, such as a Phillips drive end, a Torx drive end, or an Allen hex drive end. The key (not shown) may be inserted through the drive socket 24 of the head 20 to engage the drive end 36 of the anchor screw 14. The drive end 36 may be coaxially oriented relative to the drive socket 24. The anchor screw 14 is illustrated having a threaded body 38 along the entire axial length, though such is not required. Alternatively, the drive end 36 may be, for example, a hexagonal protrusion that is a smaller diameter than the threaded body 38.

The expandable anchor 16 is illustrated as a cylindrical structure having a bore 40 and a plurality of longitudinal slots 42 spaced around the outer surface. The bore 40 may be a slip-fit over the anchor screw 14 or may be a slight interference fit. The longitudinal slots 42 may extend axially and/or helically along the length of the anchor 16. The slots 42 define a plurality of anchor arms 44 that expand out from the anchor screw 14 when the anchor 16 is axially compressed. The outer surface of the expandable anchor 16 may be smooth or may have a surface texture 46 to aid in gripping the surrounding vertebral bone structure. In one embodiment, the surface texture may be one or more ridges 46 that extend radially out from the outer surface. Alternatively, the surface texture may be a plurality of raised dots, knurled protrusions, or screw threads.

The expandable anchor 16 is configured to be compressed between the anchor load face 32 and the nose piece 18 in order to extend the anchor arms 44. The expandable anchor 16 may be a resilient member that elastically deforms outwardly in response to the compressive load and substantially returns to its original shape when the compressive load is removed. Alternatively, the expandable anchor 16 may plastically deform outwardly and be configured to remain embedded within the vertebra V. The expandable anchor 16 may be formed from a polymer material. In one embodiment, the anchor arms 44 may be made from a polymer material having a first durometer and the one or more ridges may be made from a polymer material having a second durometer where the first durometer is softer than the second durometer. In yet another embodiment, the expandable anchor 16 may be a metallic component.

The nose piece 18 provides a leading edge of the anchoring pedicle screw assembly 10 as it is inserted into the vertebra V. The nose piece 18 is illustrated having a frusto-conical outer surface 48, a threaded aperture 50, and a load face 52. Though illustrated as having a frusto-conical shape, the nosepiece may be any shape, such as round, pointed, or diamond-shaped. The frusto-conical outer surface 48 is illustrated as smooth. However, the outer surface 48 may be fluted or otherwise textured to provide additional grip or retention within the vertebra V. The threaded aperture 50 is configured to engage the threads of the anchor screw 14. In one embodiment, the thread fit between the threaded body 38 and the threaded aperture 50 is one that may be easily brought into and out of engagement. In another embodiment, the thread fit is a torque prevailing or torque resistive fit. Alternatively, the nose piece 18 may be integrally formed onto the end of the anchor screw 14. The load face 52 of the nose piece 18 abuts one end of the expandable anchor 16 to resist the compressive force exerted by the load face 32 of the implant mounting screw 12 thus causing the anchoring arms 44 to extend outwardly. In one embodiment, the largest diameter of the nose piece 18 is smaller than the thread root 30*b* such that the nose piece 18 is easily moved within the vertebra V. In another embodiment, the largest diameter of the nose piece 18 may be the same or slightly larger than the diameter of the thread root 30*b* such that the nose piece 18 fits snugly within the vertebra V. In yet another embodiment, the largest diameter of the nose piece 18 is larger than the tooth crest 30*a*, such that the threaded section 30 does not cut or thread into the vertebra bone.

Referring now to FIGS. 4 and 5, there is illustrated a method of installing the removable anchoring pedicle screw assembly 10 into the vertebra V. Initially, an aperture A is formed into the vertebra V. The aperture A may be formed by any suitable method such as, for example, drilling and tapping. The aperture A may be sized to be smaller than the thread crest 30*a* and slightly larger than the thread root 30*b* of the main body 26. As shown in FIG. 4, the removable anchoring pedicle screw assembly 10 is inserted into the aperture A in the un-deployed state where the anchor 16 is generally cylindrical. In this condition, the anchoring arms 44 are radially drawn toward the anchor screw 14. In the illustrated embodiment of FIGS. 4 and 5 the nose piece 18 is sized in a substantial clearance fit within the aperture A. The removable anchoring pedicle screw assembly 10 may be inserted through a hole in the implant I. Alternatively, the removable anchoring pedicle screw may be inserted through a polyaxial joint (not shown) that is connected to the implant I. The implant mounting screw 12 is threaded into the vertebra V until the implant I is in position against the vertebra V. The anchor screw 14 is then adjusted to draw the nose piece 18 against the expandable anchor 16 to radially expand the anchoring arms 44 against the walls of the aperture A. In a variation of this embodiment, the threaded section 30 may include a coating to prevent the bone from fusing with the threads, thus allowing at least the implant mounting screw to be subsequently removed without undue damage. Alternatively, the anchor screw 14 may be a tight thread fit with the nose piece 18 and initially rotated to release the expandable anchor 16. Then, the entire pedicle screw assembly 10 may be extracted from the vertebra V.

In another embodiment of an installation method, the aperture A may be sized to provide a generally snug fit or "line-to-line" fit with the nose piece 18. The nose piece 18 may be a larger diameter than the thread crest 30a. The pedicle screw assembly 10 is inserted into the aperture A. The implant mounting screw 12 and the anchor screw 14 need not be rotated during insertion due to the clearance fit with the aperture A. The thread fit between the anchor screw 14 and the threaded aperture 50 of the nose piece 18 may be a generally loose or easily rotated fit. When the pedicle screw assembly 10 is sufficiently inserted into the aperture A, the anchor screw 14 is held fixed by a first tool (not shown) such as a portion of a screw driver and the implant mounting screw 12 is rotated by a coaxially oriented second tool (not shown) such as a tubular Allen wrench. As the implant mounting screw 12 is rotated relative to the anchor screw 14, the positive relative motion compresses the expandable anchor 16, thus deploying the anchoring arms 44 against the walls of the aperture A. If desired, a cement, polymer, or other filler may be injected to provide additional retention capacity, particularly for osteoporotic bones.

Figure 6:
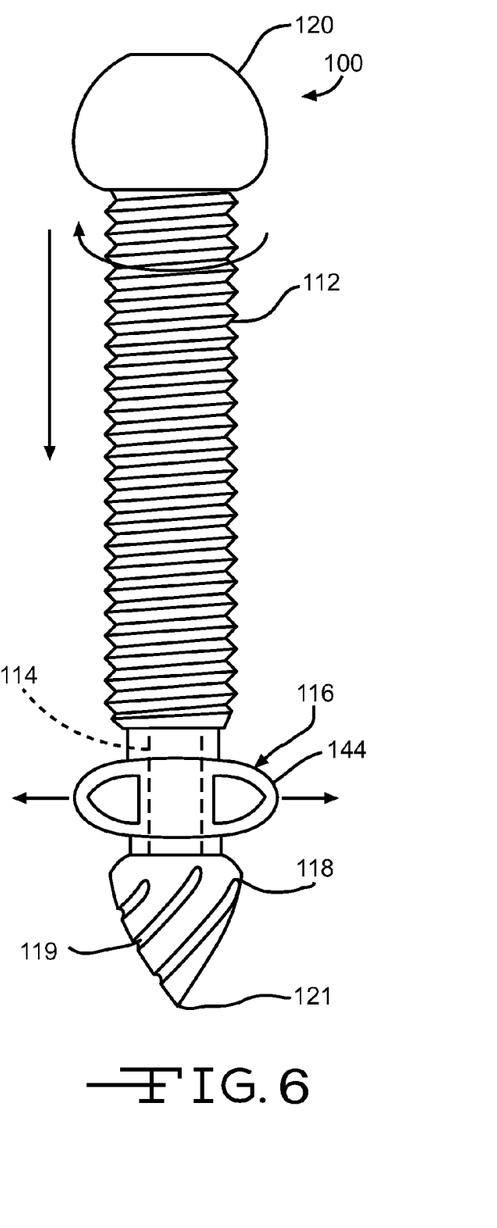
FIG. 6 is an elevational view of an embodiment of a pedicle screw assembly in a deployed configuration.

Referring now to FIG. 6, there is illustrated another embodiment of an anchoring pedicle screw 100 having an implant mounting screw 112, an anchoring screw 114, an expandable anchor 116, and a nose piece 118. The pedicle screw 100 is configured similarly to the pedicle screw 10, described above. The pedicle screw 100 is illustrated in a deployed state where the expandable anchor 116 is axially compressed between the nose piece 118 and the implant mounting screw 112 and where anchoring arms 144 are in an extended and compressed condition. The nose piece 118 is configured as a self tapping or self drilling structure. The nose piece 118 includes a plurality of flutes 119 and a pointed tip 121. The flutes 119 may be cutting flutes to simulate a drill bit or may be binding flutes that partially embed into cancellous bone and fix the nose piece 118 into the vertebra.

To remove the pedicle screw assembly 10, the implant mounting screw 12 may be removed by rotating the implant mounting screw 12 relative to the anchor screw 14. This permits the axially compressive load to be relaxed from the expandable anchor 16, allowing the anchoring arms 44 to retract or loosen from the walls of the aperture A. In the condition where bone growth has fixed the nose piece 18 to the vertebra V, the loose thread fit of the anchor screw 14 to the threaded aperture 50 permits the anchor screw 14 to be removed and the nose piece 18 to remain.

It should be understood that other relative fit variations between the aperture A, the various threaded elements and the diameter of the nose piece may permit removal of all or part of the pedicle screw assembly 10. Thus, these examples of installation and removal methods are intended to be illustrative, not exhaustive, of variations of the anchoring pedicle screw assembly 10. The anchoring pedicle mounting screw assembly 10 has a positive actuation, by way of threaded engagement, between the implant mounting screw 12 and the anchor screw 14 to effect expansion and, in certain embodiments, subsequent contraction of the expandable anchor 16 to facilitate removal.

Figure 7A:
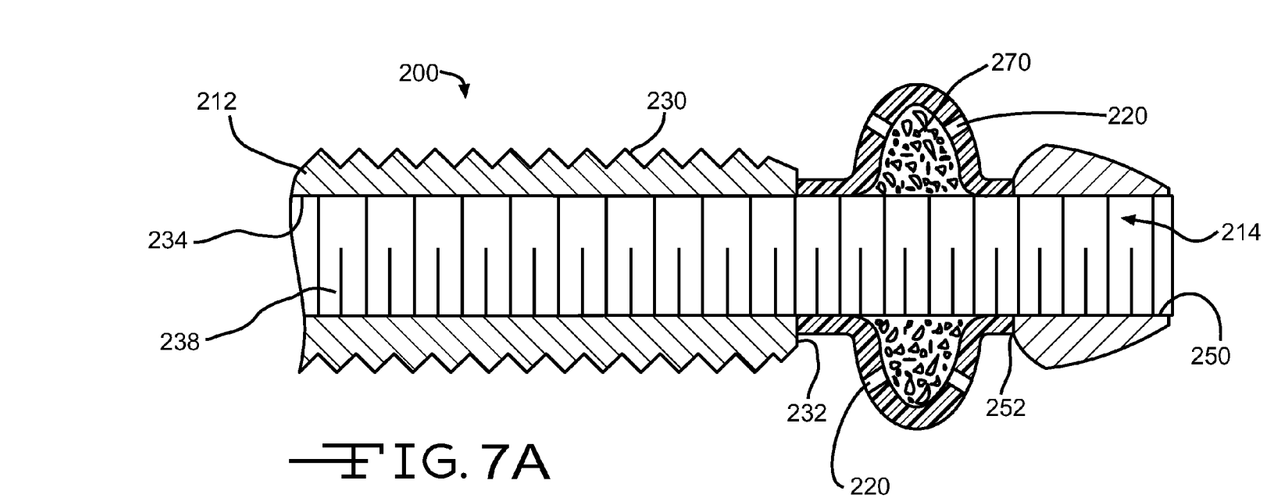
FIG. 7A is an enlarged view, in partial cross section, of a portion of another embodiment of a pedicle screw assembly.

Referring now to FIG. 7A there is schematically illustrated another embodiment of a portion of an anchoring pedicle screw assembly, shown generally at 200. The anchoring pedicle screw assembly 200 is shown in a deployed condition. An implant mounting screw 212 includes a threaded portion 230, a load face 232, and a threaded bore 234. An anchor screw 214 includes a threaded body 238 configured to engage the threaded bore 234 for relative rotation. A nose piece 218 includes a threaded aperture 250 and a load face 252. The threaded aperture 250 is configured to engage the threaded body 238 of the anchor screw 214. An embodiment of an expandable anchor 216 is disposed between the implant mounting screw load face 232 and the nose piece load face 252.

Figure 7B:
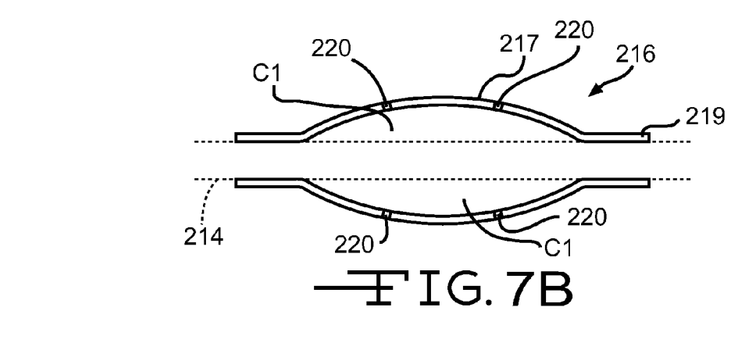
FIG. 7B is an enlarged, cross sectional view of a portion of an embodiment of an expandable anchor for use in a removable anchoring pedicle screw assembly.

In the embodiment illustrated in FIG. 7B, the expandable anchor 216, shown in the relaxed or undeployed state is a generally tubular structure having a substantially uniform wall thickness. The expandable anchor 216 has a center section 217 that gradually transitions to ends 219 that have a reduced diameter. The larger diameter center section 217 and the ends 219 cooperate to define a cavity C1 disposed about the anchor screw 214, shown in phantom. A filler 270 may be disposed within the cavity C1. The filler 270 may be bone chips to aid in bone fusion between the vertebra V and parts of the pedicle screw assembly 100. Alternatively, the filler 270 may be another medium, such as a polymer, epoxy, cement, or material having an adhesive mechanical property quality. As shown in FIG. 7A, when the expandable anchor 216 is deployed, the filler 270 is compressed. The center section 217 includes one or more purge holes 220 that permit the filler 270 to be driven into the aperture A (shown in FIGS. 4-5) as the filler 270 is compressed. In another embodiment of the expandable anchor 216, longitudinal slots (not shown) similar to slots 42 may open to permit the filler to flow into the aperture A. In yet another version of the expandable anchor 216, the center section 217 is frangible to permit the filler 270 to enter the aperture.

Figure 7C:
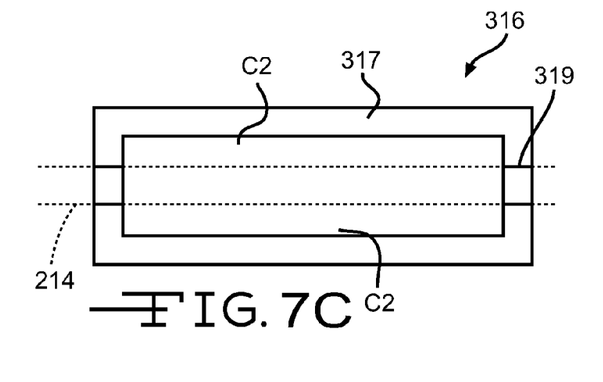
FIG. 7C is an enlarged, cross sectional view of a portion of another embodiment of an expandable anchor for use in a removable anchoring pedicle screw assembly.

Referring to FIG. 7C, another embodiment of an expandable anchor 316 is illustrated in a relaxed or undeployed state. The expandable anchor 316 includes a center section 317 and ends 319. The expandable anchor 316 is generally tubular and has a generally constant outer diameter. Similar to the embodiment above, the center section 317 and the ends 319 define a cavity C2 relative to the anchor screw 214, shown in phantom. The cavity C2 is also configured to retain the filler 270 for deployment into the aperture A.

Figure 8A:
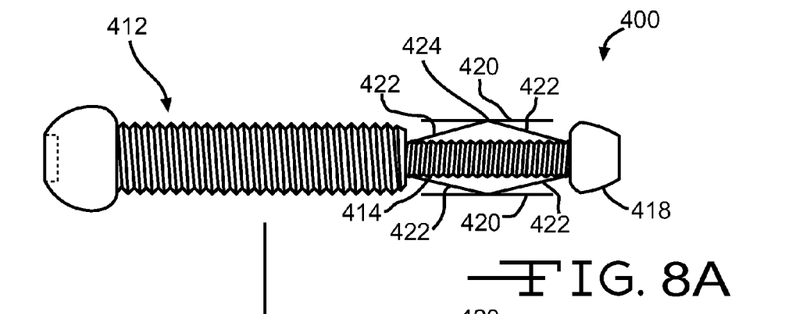
FIG. 8A is a side elevational schematic view of another embodiment of a pedicle screw assembly in an installation configuration.
Figure 8B:
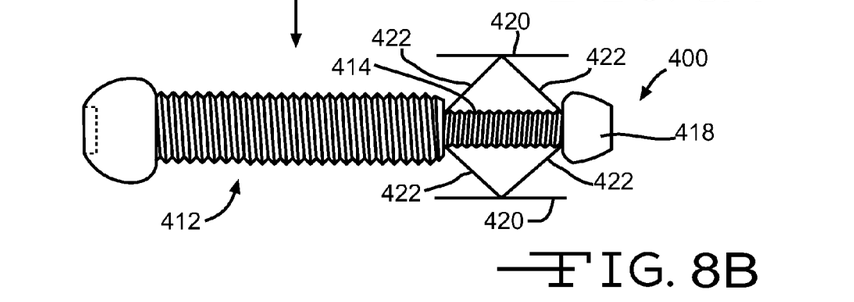
FIG. 8B is a side elevational schematic view of an embodiment of a pedicle screw assembly of FIG. 8A in a deployed condition.

Referring now to FIGS. 8A and 8B, there is illustrated another embodiment of a pedicle screw assembly, shown generally at 400. The pedicle screw 400 is illustrated in a collapsed state in FIG. 8A and in an expanded or deployed state in FIG. 8B. The pedicle screw 400 may include an implant mounting screw 412, an anchor screw 414, and a nose piece 418 that are similar to embodiments described above. The pedicle screw assembly 400 includes an expandable anchor, shown generally at 416. The expandable anchor 416 includes a plurality of spaced apart arms 420 that are generally parallel to the aperture A formed into the vertebra V. The arms 420 may be two or more arms equally spaced around the anchor screw 414. The arms 420 are pivotally connected to expansion links 422 at pivot points 424. The pivot points 424 may be configured as any type of hinge element, such as living hinges or hinges that pivot about a pin element. The expansion links 422 are positioned between the implant mounting screw 412 and the nose piece 418. The expansion links 422 may connect directly to the mounting screw 412 and nose piece 418 or connect by way of pivot points 424. Similar to the expandable anchor 16 described above, as the nose piece 418 is drawn toward the implant mounting screw 412, the compressive force drives the ends of the expansion links 422 at the screw 412 and nose piece 418 together. The expansion links force the arms 420 radially outward from the anchor screw 414 against the walls of the aperture A in the vertebra V. Additionally, the arms 420 may include teeth or any other gripping structure, similar to those described above.

Figure 8C:
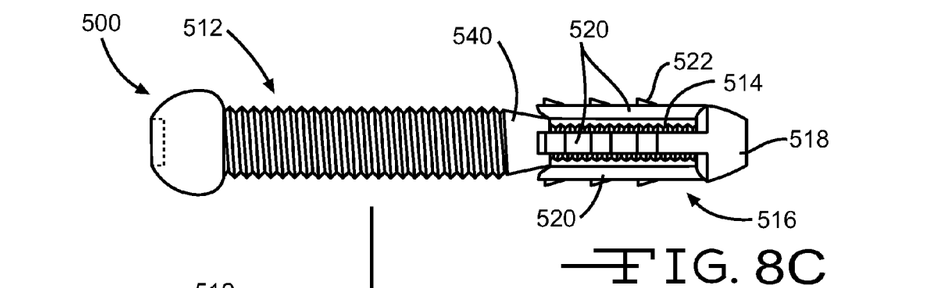
FIG. 8C is a side elevational schematic view of another embodiment of a pedicle screw assembly in an installation configuration.
Figure 8D:
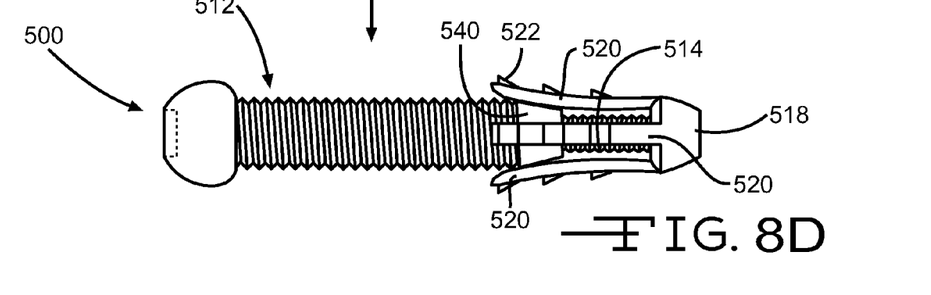
FIG. 8D is a side elevational schematic view of an embodiment of a pedicle screw assembly of FIG. 8C in a deployed condition.

Referring now to FIGS. 8C and 8D, there is illustrated another embodiment of an anchoring pedicle screw, shown generally at 500. The pedicle screw 500 is illustrated in an undeployed or collapsed state in FIG. 8C and in a deployed or expanded state in FIG. 8D. The pedicle screw 500 includes an implant mounting screw 512, an anchor screw 514, and an expansion tip 540. The implant mounting screw 512 has a threaded body 530, similar to the threaded section 30 described above. The expansion tip 540 includes a tapered profile that may be integral to the mounting screw 512 with a threaded internal diameter that accommodates the anchor screw. Alternatively, the expansion tip 540 may be a separate part that has a generally smooth bore that the anchor screw 514 passes through.

The pedicle screw 500 further includes an expandable anchor, shown generally at 516. The expandable anchor 516 includes a nose piece 518 having a plurality of resilient anchor arms 520. The resilient arms 520 extend from the nose piece 518 and may be generally parallel to the anchor screw 514, though such is not required. Alternatively, the resilient arms 520 may be connected together by another structure, such as a ring (not shown), that is positioned against the nose piece 518. The resilient arms 520 are cantilevered from the nose piece 518 to define free ends. As the nose piece 518 is moved toward the implant mounting screw 512, the free ends of the resilient arms 520 engage the tapered profile of the expansion tip 540 and are spread radially outward from the anchor screw 514. The arms 520 may include retaining barbs 522 that provide an additional grip force against the walls of the aperture A.

Figure 9:
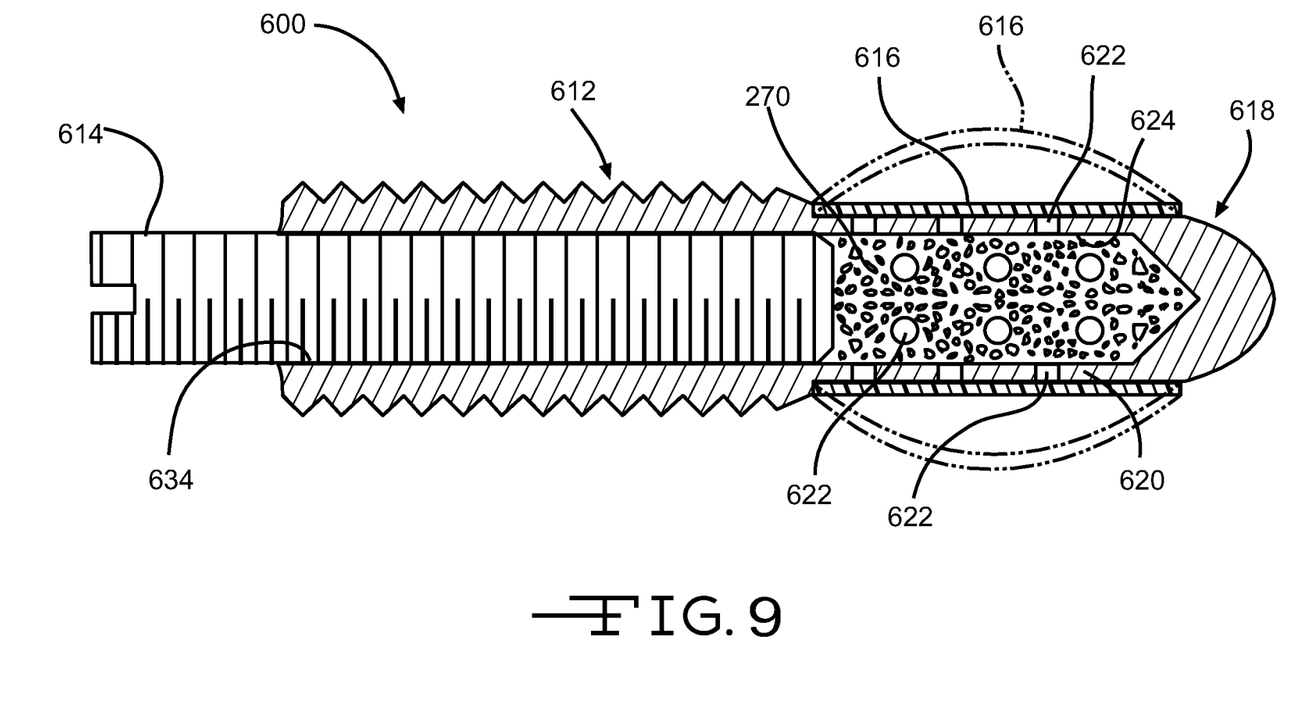
FIG. 9 is a side elevational view, in partial cross section, of a portion of another embodiment of a pedicle screw assembly.

Referring now to FIG. 9, there is illustrated another embodiment of an anchoring pedicle screw, shown generally at 600. The pedicle screw 600 includes an implant mounting screw 612. The implant mounting screw 612 may include a head portion similar to the head 20, described above. The other end of the mounting screw 612 includes a nose piece 618 that may be threaded onto the end of the implant mounting screw or may be integrally formed therewith. The pedicle screw 600 includes a plunger screw 614 that threads into a threaded bore 634 of the implant mounting screw 612 in a manner similar to the anchor screw 14, described above. The nose piece 618 includes a ported sleeve 620 having a plurality of vents 622 formed therein. A filler cavity 624 is the hollow portion of the ported sleeve 620 and is configured to hold a quantity of filler 270. An expandable anchor 616 is positioned over an outer surface of the ported sleeve 620. The expandable anchor 616 may be configured as a resilient tube, a frangible tube, or any of the expandable anchor structures described above. Prior to threading the plunger screw 614 into the implant mounting screw 612, the filler cavity 624 is filled with filler 270, such as, for example, bone chips, bone slurry, cement, or epoxy. The plunger screw 614 is then threaded into the implant mounting screw 612 and is advance into the ported sleeve 620. As the plunger screw 614 is advanced, the filler 270 is forced or extruded out of the vents 622. The filler 270 expands the expandable anchor 616 out against the walls of the aperture A. In one embodiment, the expandable anchor 616 may break open to permit the bone slurry to contact the cancellous bone of the vertebra V to encourage bone growth. In another embodiment, the expandable anchor may be a slowly dissolving material that dissolves over time to permit the filler 270 to fuse with the vertebra V.

While the invention has been described with reference to particular embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments disclosed herein contemplated for carrying out this invention, but that the invention will include all embodiments falling within the scope of the claims. The publication and other material used herein to illuminate the invention or provide additional details respecting the practice of the invention, are incorporated by reference herein.

What is claimed is:

1. An anchoring pedicle screw assembly for fixing an implant to a vertebra comprising:
   an implant mounting screw having a threaded bore;
   an anchor screw configured to engage the threaded bore for relative rotation;
   a nose piece configured to engage the anchor screw; and
   an expandable anchor disposed between the implant mounting screw and the nose piece such that rotation of the anchor screw relative to the implant mounting screw causes expansion of the expandable anchor, wherein either:
   (1) the anchor screw includes a threaded body that extends along the entire axial length of the anchor screw;
   (2) the expandable anchor cooperates with the anchor screw to define a cavity that contains a filler material;
   (3) the expandable anchor is formed from a polymer and includes at least one ridge formed from a polymer having a durometer that is different from the durometer of the rest of the expandable anchor; or
   (4) the nose piece includes a ported sleeve configured to contain a filler material and having at least one vent, and the expandable anchor is disposed over the ported sleeve such that, as the anchor screw is advanced toward the nose piece, the filler material is exhausted through the at least one vent causing the expandable anchor to expand radially outward away from the anchor screw.

2. The anchoring pedicle screw assembly of claim 1, wherein the implant mounting screw includes a first load face and the nose piece includes a second load face and a threaded aperture configured to engage the anchor screw, the first and second load faces configured to engage opposite ends of the expandable anchor such that a compressive load exerted by the first and second load faces causes the expansion of the expandable anchor.

3. The anchoring pedicle screw assembly of claim 1, wherein the expandable anchor includes a plurality of anchoring arms, the anchoring arms configured to deflect radially outwards from the anchor screw in response to rotation of the anchor screw relative to the implant mounting screw.

4. The anchoring pedicle screw assembly of claim 1, wherein the anchor screw includes a drive end and a threaded body that extends along the entire axial length of the anchor screw.

5. The anchoring pedicle screw assembly of claim 4, wherein the implant mounting screw includes a drive socket, the drive socket being coaxially oriented relative to the drive end of the anchor screw.

6. The anchoring pedicle screw assembly of claim 1, wherein the expandable anchor cooperates with the anchor screw to define a cavity.

7. The anchoring pedicle screw assembly of claim 6, wherein the cavity contains a filler material.

8. The anchoring pedicle screw assembly of claim 7, wherein the expandable anchor is a frangible structure that permits the filler material to exit the expandable anchor when compressed.

9. The anchoring pedicle screw assembly of claim 1, wherein the expandable anchor cooperates with the anchor screw to define a cavity that contains a filler material, the expandable anchor including a plurality of slots that permit the filler material to exit the expandable anchor when the expandable anchor is compressed.

10. The anchoring pedicle screw assembly of claim 1, wherein the expandable anchor is elastically deformable.

11. The anchoring pedicle screw assembly of claim 1, wherein the expandable anchor is plastically deformable.

12. The anchoring pedicle screw assembly of claim 1, wherein the expandable anchor is formed from a polymer and includes at least one ridge.

13. The anchoring pedicle screw assembly of claim 12, wherein the ridge is formed from a polymer having a durometer that is different from the durometer of the rest of the expandable anchor.

14. The anchoring pedicle screw assembly of claim 1, wherein the expandable anchor includes a bore configured to engage the anchor screw.

15. The anchoring pedicle screw assembly of claim 3, wherein the implant mounting screw includes an expansion tip having a tapered profile and the arms of the expandable anchor are cantilevered from the nose piece such that the arms are radially expanded as the expandable anchor engages the expansion tip.

16. The anchoring pedicle screw assembly of claim 1, wherein the nose piece includes a ported sleeve configured to contain a filler material and having at least one vent, and the expandable anchor is disposed over the ported sleeve such that, as the anchor screw is advanced toward the nose piece, the filler material is exhausted through the at least one vent causing the expandable anchor to expand radially outward away from the anchor screw.

17. The anchoring pedicle screw assembly of claim 1, wherein the implant mounting screw and the expandable anchor are formed from different materials.

18. An anchoring pedicle screw assembly comprising:
an anchor screw having a threaded outer surface;
an implant mounting screw including a bore having a threaded inner surface that engages the threaded outer surface of the anchor screw;
a nose piece including an aperture having a threaded inner surface that engages the threaded outer surface of the anchor screw; and
an expandable anchor disposed about the threaded outer surface of the anchor screw between the implant mounting screw and the nose piece.

19. An anchoring pedicle screw assembly comprising:
an anchor screw having an outer surface;
an implant mounting screw including a bore having an inner surface that engages the outer surface of the anchor screw;
a nose piece including an aperture having an inner surface that engages the outer surface of the anchor screw; and
an expandable anchor disposed about the outer surface of the anchor screw between the implant mounting screw and the nose piece, wherein the expandable anchor is formed from a material that is different from a material used to form either the implant mounting screw or the nose piece.

20. The anchoring pedicle screw assembly of claim 19, wherein the expandable anchor is formed from a material that is different from a material used to form both the implant mounting screw and the nose piece.

* * * * *